United States Patent [19]

Striano

[11] Patent Number: 5,207,636
[45] Date of Patent: May 4, 1993

[54] LUMBAR SPINE SUPPORT

[76] Inventor: James S. Striano, 475 Tuckahoe Rd., Ste. 201, Yonkers, N.Y. 10701

[21] Appl. No.: 879,590

[22] Filed: May 7, 1992

[51] Int. Cl.$^5$ ............................................. A61F 5/02
[52] U.S. Cl. ........................................ 602/19; 2/44
[58] Field of Search .................... 602/19, 7, 5, 61; 128/78; 606/240; 2/44

[56] References Cited

U.S. PATENT DOCUMENTS 2,828,737  4/1958  Hale ..................................... 602/19

Primary Examiner—Robert Bahr
Assistant Examiner—B. Meindl
Attorney, Agent, or Firm—Charles J. Prescott

[57] ABSTRACT

An improved lumbar spine support including an anterior and a posterior section form-fitted around the corresponding torso areas. These sections are connectable by flexible fabric panels and a strap arrangement in opposing position tightly against the torso. The anterior section includes a V-shaped indentation which hydrostatically lifts the lower abdominal musculature inwardly and upwardly. The posterior section includes an elongated upright indentation having a laterally extending wider lower portion for centering and securing the posterior section over the lumbosacral area of the spine.

4 Claims, 1 Drawing Sheet

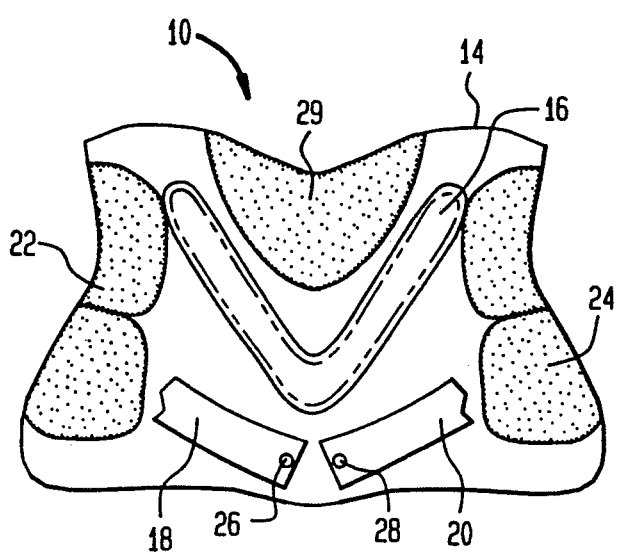
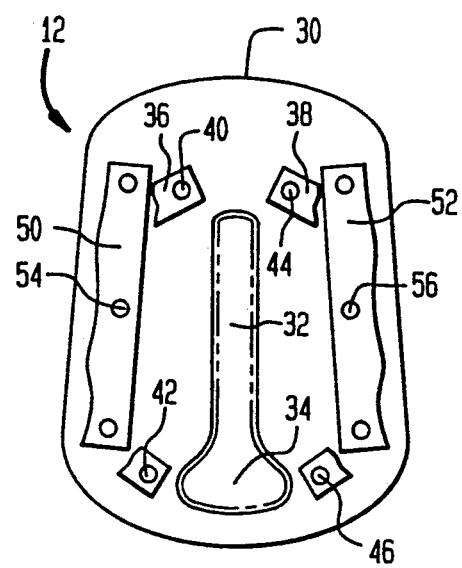
FIG. 1
FIG. 2
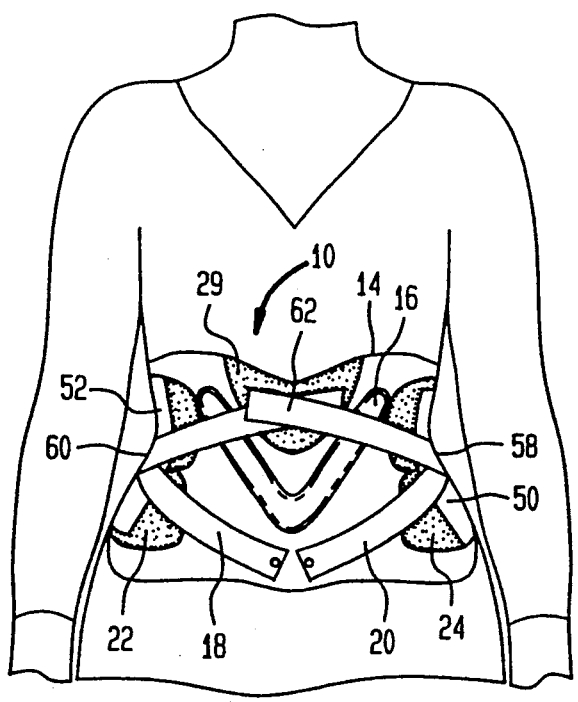
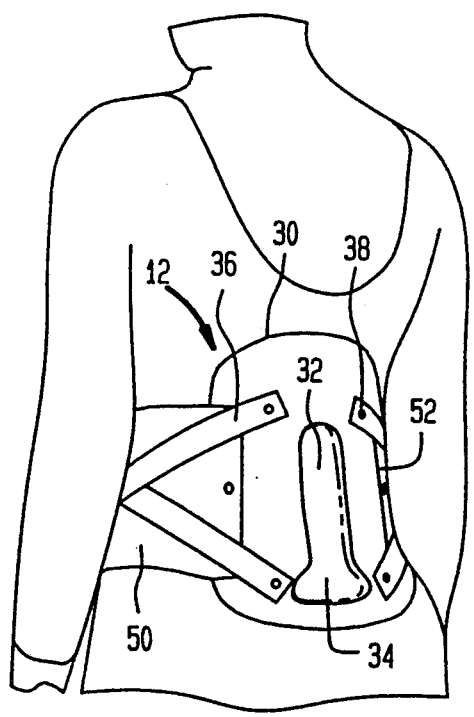
FIG. 3
FIG. 4

LUMBAR SPINE SUPPORT

BACKGROUND OF THE INVENTION

This invention relates generally to body torso supports, and more particularly to a semi or substantially rigid orthosis which provides unique lumbar centering and abdominal lifting features.

Devices in the form of rigid, semi-rigid, or flexible material constructed to at least partially surround the lower back region of the human torso are well-known for the treatment and rehabilitation of spinal disfunction. One such device is shown in U.S. Pat. No. 4,508,110 to Modglin which discloses a body jacket constructed in two parts to be laced together into a final adjusted position and then easily installed and removed thereafter.

Another device known to applicant is shown in U.S. Pat. No. 4,696,291 invented by Tyo directed to a device for treating lower back pain comprising three generally rigid members which, when properly installed, are claimed to apply a centrally directed beneficial force to the abdomen and the gluteal muscles.

Rowe in U.S. Pat. No. 4,930,499 teaches a sacral brace intended for comfortable extended wear including a rigid posterior sacral pad having a vertical central channel and connectable to an abdominal leverage plate provided for anchoring the sacral pad by tying straps.

A simple brace and method of application is disclosed in U.S. Pat. No. 5,074,292 to Cox for immobilization of various regions of the torso.

The present invention provides a lumbar spine support comprised of an anterior and posterior section asymmetrical in nature to accommodate the bony prominences known as the anterior superior iliac spine (ASIS), the iliac crest and the lumbosacral spine. The anterior section includes a central V-shaped indentation specifically structured to impress the lower abdominal musculature in such a way as to focus and compress forces exerted by the device in an upwardly and rearwardly manner known as hydrostatic lift. The posterior section includes an upright indentation with an oblong shaped transverse bottom portion conforming to the skeletal cavity created at the junction of the lumbar vertebra and the sacrum serving to guide the placement of the posterior section to insure centering over the spine and locking onto the lumbosacral area to facilitate appropriate dispersion of the resistive force of the anterior section when the adjustable closure system is tightened.

BRIEF SUMMARY OF THE INVENTION

This invention is directed to an improved lumbar spine support including an anterior and a posterior section form-fitted around the corresponding torso areas. These sections are connectable by flexible fabric panels and a strap arrangement in opposing position tightly against the torso. The anterior section includes a V-shaped indentation which hydrostatically lifts the lower abdominal musculature inwardly and upwardly. The posterior section includes an elongated upright indentation having a laterally extending wider lower portion for centering and securing the posterior section over the lumbosacral area of the spine.

It is therefore an object of this invention to provide an improved lumbar spine support which combines the biomechanical advantages of an asymmetrical clam shell support with the comfort and convenience of an elasticized and fully adjustable closure system.

It is yet another object of this invention to provide a lumbar spine support which causes hydrostatic lift to occur in the abdominal cavity to relieve the pressure on and to allow equalization of, the discs of the spine.

It is yet another object of this invention to provide a lumbar spine support which, by hydrostatic lift, overcomes the forces of gravity and resists reversing chiropractic adjustments caused by twisting, turning or poor ergonomics.

It is yet another object of this invention to provide a lumbar spine support which is firmly self-positioning on the ASIS, the iliac crest, and the lumbosacral spine to control lumbosacral rotation, thus lessening the possibility of reinjury during healing.

It is yet another object of this invention to provide a lumbar spine support which will adequately support the spine while permitting exercising of the underlying musculature and is of an ultra thin construction to facilitate undergarment wear.

In accordance with these and other objects which will become apparent hereinafter, the instant invention will now be described with reference to the accompanying drawings.

BRIEF DESCRIPTION OF THE DRAWINGS

FIG. 1 is a front elevation view of the anterior section of this invention.

FIG. 2 is a rear elevation view of the posterior section of this invention.

FIG. 3 is a pictorial view of the invention in use as viewed from the front of a patient.

FIG. 4 is a pictorial view of the invention in use as viewed from the rear of a patient.

DETAILED DESCRIPTION OF THE INVENTION

Referring now to the drawings, the invention includes an anterior section 10 and a posterior section 12. Both sections 10 and 12 include anterior and posterior shells 14 and 30, respectively, which are fabricated of a contour molded sheet of thermoplastic material forming the outer layer thereof adhered to an inner layer of compressible closed cell foam forming the inner surface thereof. Each of these shells 14 and 30 are semi-rigid in that some flexure is possible to improve fit and comfort during normal body movement.

In FIGS. 1 and 3, the anterior section 10 includes a V-shaped indentation 16 disposed centrally across the frontal surface of shell 14. This indentation 16 is inwardly formed into the thermoplastic outer shell, the inner closed cell foam layer conforming thereto, and is structured so as to be positioned in the vicinity of the abdominal cavity whereby compression forces exerted by the anterior section 10, when suitably attached to the posterior section 12 as will be described herebelow, are directed upwardly and rearwardly to produce hydrostatic lift of the abdomen area of the wearer.

The posterior section 12 includes an elongated, upright indentation 32 formed inwardly into the thermoplastic outer layer of shell 30, the adhered closed cell foam inner layer conforming thereto. This indentation 32 includes a lower elongated transverse portion 34, the combination structured, when the posterior shell 30 is position as shown in FIG. 4, to guide the placement of the posterior section 12 for proper centering over the spine to conform to the skeletal cavity created or the junction or the lumbar vertebra and the sacrum and to lock onto the lumbosacral area of the spine for even dispersion of the resistive force when tightly strapped to the anterior section 10 around the torso of the user.

The anterior and posterior sections 10 and 12 are initially positioned around the torso as shown in FIGS. 3 and 4 and thereafter, flexible fabric panels 50 and 52, riveted at 54 and 56, respectively, to adjacent the lateral edges of the posterior section 12, are drawn forwardly to be adhered by a hook and loop arrangement onto the anterolateral regions 22 and 24 of the anterior section 14.

With the anterior and posterior sections 10 and 12 in place, a tensioning strap arrangement is also provided to increase the compressive forces exerted against the torso by indentations 16 and 32. This strap arrangement includes first flexible fabric straps 36 and 38 connected at each end by rivets 40/42 and 44/46, respectively onto the posterior shell 30 as best seen in FIG. 2. These first straps 36 and 38 loosely extend from each rivet connection to wrap partially around the outer surface of the flexible panels 50 and 52, respectively. Each of these straps 36 and 38 includes a ring 58 and 60, respectively, slidably connected therearound.

The strap arrangement also includes a pair of second straps 18 and 20 which are connected at one end by rivets 26 and 28 onto the central lower region of anterior shell 14 as best seen in FIG. 1. These second straps 18 and 20 are separately threadably engagable through rings 58 and 60 and, thereafter, manually tensionable in criss cross fashion at 62 in FIG. 3 across the upper region of the anterior section and, by hook and pile arrangement, are connectable at 20 onto the anterior shell 14.

By this arrangement, the user may grasp the free ends of each of the second straps 18 and 20 and, pulling them in opposing criss cross diagonal fashion, tensioning these second straps 18 and 20 to an appropriate level and, thereafter, releasably adhering the ends thereof onto region 29.

By appropriate tensioning as above described, the V-shaped indentation 16 is impressed into the abdominal region to hydrostatically lift this area of the torso inwardly and upwardly so as to relieve tension on the discs of the spine. Again, the upright indentation 32 of the posterior shell 30 serves to center and align the entire arrangement both rotationally and vertically so as to insure proper positioning of the V-shaped indentation 16.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A lumbar spine support comprising:
 a substantially rigid, body contoured, anterior section having lateral edges which terminate in the right and left anterolateral regions of the torso;
 a substantially rigid, body contoured, posterior section having lateral edges which terminate in the right and left posterolateral regions of the torso;
 flexible side panels connectable between corresponding said lateral edges of said anterior and posterior sections structured for holding said anterior and posterior sections in opposing relationship against the corresponding anterior and posterior areas, respectively, of the torso;
 strap means connectable between corresponding said lateral edges of said anterior and posterior sections for adjustably tightening said anterior and posterior sections together against the torso;
 said anterior section including a central V-shaped indentation positioned and structured to hydrostatically lift the lower abdominal musculature of the torso inwardly and upwardly;
 said posterior section including an elongated central upright indentation having a laterally extending portion at the lower end thereof and positioned and structured to center and secure said posterior section over the lumbosacral area of the spine.

2. A lumbar spine support as set forth in claim 1, wherein:
 said anterior and posterior sections are formed of an outer sheet of thermoplastic connected to an inner layer of closed cell foam.

3. A lumbar spine support as set forth in claim 1, wherein:
 said upright indentation is structured, in cooperation with said posterior section, to conform to the skeletal cavity created at the junction of the lumbar vertebra and the sacrum.

4. A lumbar spine support comprising:
 a semi-rigid, body contoured, anterior section having lateral edges which terminate in the right and left anterolateral regions of the torso;
 a semi-rigid, body contoured, posterior section having lateral edges which terminate in the right and left posterolateral regions of the torso;
 flexible fabric side panels connectable between corresponding said lateral edges of said anterior and posterior sections structured for holding said anterior and posterior sections in opposing relationship against the corresponding anterior and posterior areas, respectively, of the torso;
 strap means connectable between corresponding said lateral edges of said anterior and posterior sections for adjustably tightening said anterior and posterior sections together against the torso;
 said anterior section including a central V-shaped indentation positioned and structured to hydrostatically lift the lower abdominal musculature of the torso inwardly and upwardly when said strap means is tightened;
 said posterior section including an elongated central upright indentation having a laterally extending lower portion and positioned and structured to center and secure said posterior section over the lumbosacral area of the spine;
 said upright indentation structured, in cooperation with said posterior section, to conform to the skeletal cavity created at the junction of the lumbar vertebra and the sacrum;
 said anterior and posterior sections formed of an outer sheet of thermoplastic adhered to and coextensive with an inner layer of closed cell foam.

* * * * *